United States Patent

Mineta et al.

[11] Patent Number: 5,840,209
[45] Date of Patent: Nov. 24, 1998

[54] OPTICALLY ACTIVE COMPOUND, LIQUID CRYSTAL COMPOSITIONS CONTAINING THE OPTICALLY ACTIVE COMPOUND, AND LIQUID CRYSTAL DISPLAY DEVICE

[75] Inventors: Hiroshi Mineta; Tomoyuki Yui; Masahiro Johno; Seiji Adachi; Yuki Motoyama, all of Tsukuba, Japan

[73] Assignee: Mitsubishi Gas Chemical Company, Inc., Tokyo, Japan

[21] Appl. No.: 856,285

[22] Filed: May 14, 1997

[30] Foreign Application Priority Data

May 14, 1996 [JP] Japan ..................................... 8-118757
Jul. 9, 1996 [JP] Japan ..................................... 8-179378

[51] Int. Cl.$^6$ ........................... C09K 19/20; C07C 69/76; C07C 41/00; G02F 1/1343
[52] U.S. Cl. ................................ 252/299.67; 252/299.01; 252/299.64; 252/299.65; 252/299.66; 560/65; 560/83; 568/647; 349/143; 349/172; 349/174; 349/182
[58] Field of Search ........................ 252/299.01, 299.64, 252/299.65, 299.66, 299.67; 560/65, 83; 568/647; 349/182, 143, 172, 174

[56] References Cited

U.S. PATENT DOCUMENTS

| 5,292,453 | 3/1994 | Shinjo et al. | 252/299.61 |
| 5,352,382 | 10/1994 | Johno et al. | 252/299.65 |

FOREIGN PATENT DOCUMENTS

| 0341686 | 11/1989 | European Pat. Off. . |
| 0517504 | 12/1992 | European Pat. Off. . |
| 0562627 | 9/1993 | European Pat. Off. . |
| 0582468 | 2/1994 | European Pat. Off. . |
| 5150257 | 6/1993 | Japan . |
| 5249502 | 9/1993 | Japan . |
| 695080 | 4/1994 | Japan . |
| 07-242601 | 9/1995 | Japan . |

OTHER PUBLICATIONS

WPIDS 95–355218, 1995.
Japanese Journal of Applied Physics, vol. 27, No. 5, 9–L 732, May 1988.
Japanese Journal of Applied Physics, vol. 28, No. 7, pp. L1261–L1264, Jul. 1989.
Japanese Journal of Applied Physics, vol. 28, No. 7, pp. L1265–L1268, Jul. 1989.
Japanese Journal of Applied Physics, vol. 28, No. 1, pp. L119–L 120, Jan. 1989.
Japanese Journal of Applied Physics, vol. 29, No. 1, pp. L111–L114, Jan. 1990.
Reprints of the 4th Ferroelectric Liquid Crystal Symposium, pp. 77–78, 1993.
Japanese Journal of Applied Physics, vol. 30, No. 8, pp. 1759–1764, Aug. 1991.
Nito et al, TFT–driven Monostable Ferroelectric Liquid Crystal Display with Wide Viewing Angle and Fast Response Times, preprint pp. 48–51, SID'94.

*Primary Examiner*—Shean C. Wu
*Attorney, Agent, or Firm*—Sherman and Shalloway

[57] ABSTRACT

[I] An optically active compound of the formula (1),

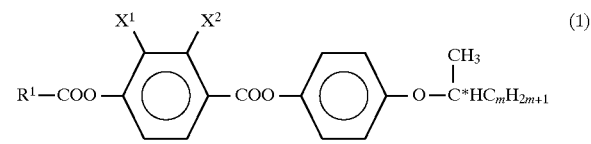

wherein $R^1$ is a linear alkyl group, each of $X^1$ and $X^2$ is a hydrogen atom or one of $X^1$ and $X^2$ is a hydrogen atom and the other is a fluorine atom, each of $Y^1$ and $Y^2$ is a hydrogen atom or one of $Y^1$ and $Y^2$ is a hydrogen atom and the other is a fluorine atom, m is an integer of 3 to 10, and C* is an asymmetric carbon atom,

[II] an anti-ferroelectric liquid crystal composition consisting essentially of the optically active compound of the above formula (1) and a compound of the formula (2),

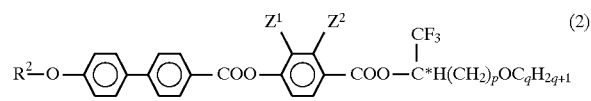

and

[III] a ferrielectric liquid crystal composition consisting essentially of the optically active compound of the formula (1) and a compound of the formula (3).

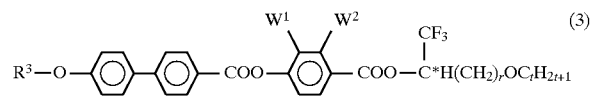

22 Claims, 1 Drawing Sheet

OPTICALLY ACTIVE COMPOUND, LIQUID CRYSTAL COMPOSITIONS CONTAINING THE OPTICALLY ACTIVE COMPOUND, AND LIQUID CRYSTAL DISPLAY DEVICE

FIELD OF THE INVENTION

The present invention relates to an optically active compound having a specific structure and liquid crystal compositions containing the compound. More specifically, it relates to a novel optically active compound useful as a component for a liquid crystal composition and two types of liquid crystal compositions containing the compound. One of the two types of the liquid crystal compositions refers to an anti-ferroelectric liquid crystal composition, and the other refers to a ferrielectric liquid crystal composition. Further, the present invention relates to a simple matrix liquid crystal display device and an active matrix liquid crystal display device both of which use the above liquid crystal compositions.

PRIOR ART

A liquid crystal display device (LCD) has been so far applied to various small-sized display devices owing to its low-voltage operability, low power consumption and thin display. With recent broadening of application and use of liquid crystal display devices to/in an information and office automation-related machine and equipment field and a television field, there are rapidly growing demands for high-performance, large-sized liquid crystal display devices having higher display capacity and higher display quality over existing CRT display devices.

Meanwhile, a liquid crystal display device as a flat panel display is already superseding a conventional Braun tube display (CRT) mainly in the fields of portable machines and equipment. With the recent functional extension of personal computers and word processors and with the recent increase in the volume of data processing, LCD is as well required to have higher functions such as a higher display capacity, full-color display, a wide viewing angle, a high-speed response and a higher contrast.

However, as long as a nematic liquid crystal available at present is used, even an active matrix-driven liquid crystal display device used in a liquid crystal television set finds it not easy to increase its size and decrease its production cost due to its complicated production process and low yield. In a simple matrix-driven STN liquid crystal display device, large display capacity driving is not necessarily easy and its response time is limited, so that video frame rate display is therefore difficult. Further, a display device using a nematic liquid crystal is beginning to find a serious problem in its narrow viewing angle.

At present, therefore, it cannot be said that a nematic liquid crystal display device can satisfy demands toward the above a high-performance large-sized liquid crystal display device.

Under the circumstances, it is a liquid crystal display device for which a ferroelectric liquid crystal is adapted that is attracting attention as a high-response liquid crystal display device. A surface stabilized ferroelectric liquid crystal (SSFLC) device disclosed by Clark and Lagerwall attracts attention in that it has a fast response and a wide viewing angle which have not been achieved in the past. Its switching characteristics have been studied in detail, and a number of ferroelectric liquid crystal compounds have been synthesized for optimizing various physical property constants. However, it has problems that its threshold characteristic is insufficient, that its contrast is low since its layer has a chevron structure, that the fast response is not achieved as is expected, that alignment control is difficult so that it is not easy to obtain the bistability which is one of the greatest characteristics of SSFLC, and that alignment destroyed by mechanical shock is difficult to restore. It is therefore required to overcome these problems for its practical use.

In addition to the above, the development of devices having switching mechanisms different from that of SSFLC are also under way. Switching among tristable states of a liquid crystal substance having an anti-ferroelectric phase (to be referred to as "anti-ferroelectric liquid crystal substance" hereinafter) is also one of these new switching mechanisms (Japanese Journal of Applied Physics, Vol. 27, pp. L729, 1988).

As described above, an anti-ferroelectric liquid crystal device has three stable states, i.e., two uniform states (Ur, Ul) observed in a ferroelectric device and a third state. Chandani et al reports that the above third state is an anti-ferroelectric phase (Japanese Journal of Applied Physics, vol. 28, pp. L1261, 1989 and Japanese Journal of Applied Physics, vol. 28, pp. L1265, 1989).

The above switching among tristable states is the first characteristic of an anti-ferroelectric liquid crystal device. The second characteristic of the anti-ferroelectric liquid crystal device is that a sharp threshold value is present relative to an applied voltage. Further, it has a memory effect, which is the third characteristic of the anti-ferroelectric liquid crystal device. By utilizing these excellent characteristics, a simple matrix-driven liquid crystal display device having a fast response and a good contrast can be achieved.

The anti-ferroelectric liquid crystal has another great characteristic in that its layer structure easily performs switching when an electric field is applied (Japanese Journal of Applied Physics, Vol. 28, pp. L119, 1989 and Japanese Journal of Applied Physics, vol. 29, pp. L111, 1990).

On the basis thereof, a liquid crystal display device free of defects and capable of self-restoring alignment can be produced, and a liquid crystal device having an excellent contrast can be achieved.

Further, it has been demonstrated that analogue gradation caused by applied voltage, which is almost impossible for a ferroelectric liquid crystal device, is possible for an anti-ferroelectric liquid crystal device. Accordingly, it is made possible to shift toward a full-color display, and the importance of an anti-ferroelectric liquid crystal device is increasing (Preprints of The 4th Ferroelectric Liquid Crystal International Symposium, page 77, 1993).

As described above, the anti-ferroelectric liquid crystal device is gaining reliable dominance, while it is desired to broaden a driving temperature range and further improve its response speed, and it is further desired to develop an anti-ferroelectric liquid crystal device having a smectic A phase.

With regard to the response speed, there is a serious problem on a low-temperature side, particularly on the side of temperatures lower than room temperature.

Practically, the response speed on the side of a low-temperature, e.g., at 10° C., is as low as $1/10$ to $1/20$ of that at room temperature. Attempts are therefore being made to change frequency or a driving voltage or to install a heater for the purpose of making the driving smoother on a low-temperature side. However, the changing of the frequency or the voltage has its limitation and has not yet fully compensated the poor characteristics of the liquid crystal.

Further, when a heater is installed, the device shows a decrease in transmittance so that the contrast decreases. As a result, a device having a high display quality can not be expected to obtain.

The anti-ferroelectric liquid crystal device has two switching processes, one from an anti-ferroelectric state to a ferroelectric state and the other from a ferroelectric state to an anti-ferroelectric state. The speeds of these two switching processes based on voltage, i.e., response speeds, are important factors for determining a display quality.

The response speed from an anti-ferroelectric state to a ferroelectric state (to be referred to as "response speed I" hereinafter) is important since it is, for example, an addressing speed multiplexing driving so that it determines the number of scanning lines which constitute one frame in simple matrix driving of consecutive scanning. That is, as the response speed I increases, the number of scanning lines can be increased, so that a high-resolution device can be achieved.

Further, concerning the response speed from a ferroelectric state to an anti-ferroelectric state (to be referred to as "response speed II" hereinafter), a required speed varies depending upon a design of a driving method of the device. For example, it alters according to the set voltage of an offset voltage. However, when the response speed II is too fast, a ferroelectric state can not be fully maintained (a light or dark state cannot be maintained), while when it is too slow, disadvantageously, no change from a ferroelectric state to an anti-ferroelectric state takes place (no rewriting from a light or dark state to a dark or light state can be performed). For the response speed II, an optimum response speed is set after a driving method is determined.

As explained above, a fast response speed I is important for achieving a high-resolution device, and at the same time, it is preferred that the dependency of the response speed on temperature be low.

Practically, the anti-ferroelectric liquid crystal device is desired to have a further improved response speed on a low temperature side, a broadened temperature range of an anti-ferroelectric phase and a presence of a smectic A phase.

M. Nakagawa has shown that the response speed of an anti-ferroelectric liquid crystal depends upon the rotation viscosity of liquid crystal molecules (Masahiro Nakagawa, Japanese Journal of Applied Physics, 30, 1759 (1991)). That is, with a decrease in viscosity, the response speed increases.

Further, when the response speed relative to temperature is observed, the response speed starts to become slow around room temperature and lowers exponentially in the temperature range lower than room temperature. An anti-ferroelectric liquid crystal has a high viscosity since its liquid crystal phase is a smectic phase, so that its viscosity sharply increases on a low-temperature side, and it is presumed that the response speed sharply becomes slow due to the viscosity resistance thereof.

In one specific method for overcoming the above problem, it is conceivable to make an attempt to improve the response speed by adding a compound having a relatively low viscosity to a liquid crystal composition to decrease the viscosity of the composition as a whole, and this method is considered to be the most practical solution at present. However, this method tends to drop the upper limit temperature of the anti-ferroelectric phase, and it poses a problem in respect of the temperature range of the anti-ferroelectric phase although the response speed is improved.

When it is considered to use an anti-ferroelectric liquid crystal as a display, generally, the temperature of the device increases up to about 40° C. due to the heat of backlight. For normal driving of the device, therefore, the upper-limit temperature of the anti-ferroelectric phase is required to be at least 40° C., and for obtaining excellent alignment, it is desired that a smectic A phase exists on the side of temperatures higher than this temperature.

Further, on the low-temperature side, the device is required to be driven at at least 10° C., and hence, the lower-limit temperature of the anti-ferroelectric phase is required to be at least 0° C.

SUMMARY OF THE INVENTION

The present invention in one aspect has been made from the above points of view, and it is an object of the present invention to provide an anti-ferroelectric liquid crystal composition which secures an anti-ferroelectric phase in a wide temperature range and which exhibits an extremely fast response at a low temperature; and a liquid crystal display device thereof.

It is another object of the present invention to provide an optically active compound as a component for the above anti-ferroelectric liquid crystal composition.

According to studies by the present inventors, the above object of the present invention is achieved by an optically active compound of the formula (1), wherein $R^1$ is a linear alkyl group, each of $X^1$ and $X^2$ is a hydrogen atom or one of $X^1$ and $X^2$ is a hydrogen atom and the other is a fluorine atom, m is an integer of 3 to 10, and $C^*$ is an asymmetric carbon atom.

The present inventors have made further studies, and as a result, have found that the object of the present invention is achieved by an anti-ferroelectric liquid crystal composition containing an optically active compound of the formula (1) and an anti-ferroelectric liquid crystal compound of the formula (2), wherein, in the formula (1), $R^1$, $X^1$, $X^2$ and m are as defined in the above formula (1), and in the formula (2), $R^2$ is a linear alkyl group, each of $Z^1$ and $Z^2$ is a hydrogen atom or one of $Z^1$ and $Z^2$ is a hydrogen atom and the other is a fluorine atom, p is an integer of 5 to 8, q is an integer of 2 or 4, and $C^*$ is an asymmetric carbon atom.

DETAILED DESCRIPTION OF THE INVENTION

The optically active compound and the anti-ferroelectric liquid crystal composition containing it, provided by the present invention, will be explained in detail hereinafter.

In the optically active compound of the formula (1), $R^1$ is a linear alkyl group, preferably a linear alkyl group having 6 to 12 carbon atoms. Each of $X^1$ and $X^2$ is a hydrogen atom, or one of these is a hydrogen atom and the other is a fluorine atom. In the latter case, preferably, $X^1$ is a hydrogen atom and $X^2$ is a fluorine atom. m is an integer of 3 to 10, preferably 3 to 8. C* is an asymmetric carbon atom.

The optically active compound of the present invention can be easily produced by the following method.

The method is outlined as follows.

(a) R*OH+p—TsCl→R*OTs (b) Compound from (a)+p—HO—Ph—O—CH$_2$Ph →PhCH$_2$—O—Ph—O—R*

(c) Compound from (b)+H$_2$→HOPhO—R*

(d) $R^1$COO—Ph—COOH+SOCl$_2$→$R^1$COO—Ph—COCl (e) Compound from (d)+Compound from (c) →Optically active compound In the above (a) to (e), R*OH is an optically active 2-alkanol, p-TsCl is p-toluenesulfonyl chloride, Ph is a 1,4-phenylene group (which may be substituted with fluorine in the 2- or 3-position), and PhCH$_2$— is a benzyl group. $R^1$ is as defined in the formula (1).

The above production method will be briefly explained below.

(a) Tosylation of optically active alcohol.

(b) Reaction of a compound from (a) with p-benzyloxyphenol.

(c) Hydrogenation of a compound from (b) to eliminate a benzyl group.

(d) Chlorination of 4-carbonyloxybenzoic acid.

(e) Reaction between a compound from (d) and a compound from (c) to synthesize an optically active compound as an end product.

In the anti-ferroelectric liquid crystal compound of the above formula (2), $R^2$ is a linear alkyl group, preferably a linear alkyl group having 6 to 10 carbon atoms. Each of $Z^1$ and $Z^2$ is a hydrogen atom, or one of these is a hydrogen atom and the other is a fluorine atom. In preferred embodiments of $Z^1$ and $Z^2$, $Z^1$ is a hydrogen atom and $Z^2$ is a fluorine atom. p is an integer of 5 to 8, preferably 5. q is an integer of 2 or 4, preferably 2.

In the anti-ferroelectric liquid crystal composition of the present invention, the proportions of the optically active compound of the formula (1) and the anti-ferroelectric liquid crystal compound of the formula (2) are 5 to 40 mol % and 95 to 60 mol %, preferably 10 to 30 mol % and 90 to 70 mol %, respectively.

In the anti-ferroelectric liquid crystal composition of the present invention, the upper-limit temperature of the anti-ferroelectric phase is preferably at least 40° C. in view of a temperature increase of the liquid crystal device caused by the heat of backlight. Further, since the liquid crystal device is required to be operable in the neighborhood of 10° C., desirably, the lower-limit temperature of the anti-ferroelectric phase is present at at least 0° C.

Further, the anti-ferroelectric liquid crystal composition of the present invention preferably has a smectic A phase present on a higher temperature than that of the anti-ferroelectric phase in view of the alignment properties.

The anti-ferroelectric liquid crystal composition of the present invention is interposed between substrates having scanning electrodes and signal electrodes arranged in a matrix form, and used as a simple matrix liquid crystal display device. In this display device, the driving by voltage can be switched among one anti-ferroelectric state and two ferroelectric states by a simple matrix driving method.

The anti-ferroelectric liquid crystal compound of the formula (2) used in the present invention can be easily produced, for example, by the following method.

(i) AcO—Ph(2X)—COOH+SOCl$_2$→AcO—Ph(2X)—COCl (ii) Compound from (i)+HOC*H(CF$_3$)—(CH$_2$)$_p$OC$_q$H$_{2q+1}$→AcO—Ph(2X)—COO—C*H(CF$_3$)—(CH$_2$)$_p$OC$_q$H$_{2q+1}$ (iii) Compound from (ii)+(Ph—CH$_2$NH$_2$) →HO—Ph(2X)—COO—C*H(CF$_3$)—(CH$_2$)$_p$OC$_q$H$_{2q+1}$ (iv) $R^2$O—Ph—Ph—COOH+SOCl$_2$→$R^2$O—Ph—Ph—COCl (v) Compound from (iii)+compound from (iv) →Anti-ferroelectric liquid crystal compound In the above (i) to (v), Ph is a 1,4-phenylene group, Ph(X) is a 1,4-phenylene group (which maybe substituted with fluorine on the 2- or 3-position), Ac is an acetyl group, and $R^2$, p and q are as defined in the formula (2).

The above production method will be briefly explained below.

(i) Formation of an acid chloride by the chlorination of fluorine-substituted or non-substituted p-acetoxybenzoic acid with thionyl chloride.

(ii) Formation of an ester by a reaction of the acid chloride (i) with an optically active alcohol.

(iii) Deacetylation of the ester from (ii).

(iv) Formation of an acid chloride of alkyloxybiphenyl-carboxylic acid.

(v) Formation of a liquid crystal compound by a reaction of a compound from (iii) with the acid chloride from (iv).

As explained above, the present invention provides the novel optically active compound (formula (1)), and further provides an anti-ferroelectric composition containing the above optically active compound. This anti-ferroelectric composition has an anti-ferroelectric phase in a broad temperature range and exhibits a fast response at temperatures lower than room temperature. There can be therefore obtained an anti-ferroelectric liquid crystal display device having a high display quality.

The present inventors have made further studies, and as a result, have found that a composition prepared by blending the optically active compound of the above formula (1) with a specific ferrielectric liquid crystal compound has excellent characteristics as an active matrix liquid crystal display device.

A conventional ferrielectric liquid crystal display device will be explained below, and thereafter, the ferrielectric liquid crystal composition and the ferrielectric liquid crystal display device, provided by the present invention, will be explained.

As a liquid crystal display mode (liquid crystal driving method) having higher functions such as higher display capacity, full-color display, wide viewing angle and high-speed response over a conventional liquid crystal display device (LCD), there has been proposed and practically used an active matrix (AM) display device which works by a method in which thin film transistors (TFT) or diodes (MIM) are formed such that one transistor or diode corresponds to one pixel on a display screen and a liquid crystal is driven for each pixel independently of every other one. The above display mode has problems in that it is difficult to decrease a cost due to a low yield and that it is difficult to provide a large display screen. However, due to a high display quality, the above display mode is about to surpass an STN method which has been a conventional mainstream and to overtake CRT.

However, the above AM display device has the following problems since it uses a TN (twisted nematic) liquid crystal as a liquid crystal material.

(1) A TN liquid crystal is a nematic liquid crystal, and the response speed is generally low (tens ms). In the display of video frame rate, no good display quality can be obtained.

(2) A twisted state (twist alignment) of liquid crystal molecules is used for displaying, and the viewing angle is therefore narrow. In a gray-scaling display in particular, the viewing angle is sharply narrowed. That is, the contrast ratio and the color change depending upon viewing angles to a display screen.

For overcoming the above problems, in recent years, there have been proposed AM panels which use a ferroelectric liquid crystal or an anti-ferroelectric liquid crystal in place of the TN liquid crystal (Japanese Laid-open Patent Publications Nos. 249502/1993, 150257/1993 and 95080/1994). However, these AM panels have the following problems, which constitute practically barriers against putting them into practical use.

(1) A ferroelectric liquid crystal has spontaneous polarization. An image sticking is liable to take place due to a constant presence of the spontaneous polarization, and the driving is made difficult. In a display by a surface-stabilized mode, it is very difficult to perform a gray-scaling display since only a binary display of black and white is possible. For a gray-scaling display, a special devising is required (e.g., ferroelectric liquid crystal device using monostability); Keiichi NITO et al., SID '94, Preprint, p.48), and it is required to develop a very high technique for practical use.

(2) An anti-ferroelectric liquid crystal is free of the problem of image sticking described in the above (1) since it has no permanent spontaneous polarization.

Meanwhile, the AM driving requires a liquid crystal material which can be driven at a low voltage of at least 10V or less. However, the anti-ferroelectric liquid crystal generally shows a high threshold voltage, and it is therefore difficult to drive at a low voltage. Further, it has a problem that a gray-scaling display is difficult since its optical response involves a hysteresis.

It is an object of the present invention to provide a novel material which can overcome the above problems and is suitable for AM driving. A ferrielectric liquid crystal is conceivable as the above novel material.

A ferrielectric phase (SCγ* phase)was found in 4-(1-methylheptyloxycarbonyl)phenyl 4-(4-octyloxyphenyl) benzoate (to be abbreviated as "MHPOBC" hereinafter) in 1989 for the first time (Japanese Journal of Applied Physics, Vol. 29, No. 1, 1990, pp. L131–137).

MHPOBC has the following structural formula and phase sequence.

Structure formula:

wherein Ph is a phenylene group and C* is an asymmetric carbon atom.

Phase sequence:
Cr(30)SIA*(65)SCA*(118)SCγ*(119)SC*(121)SCα*(122)SA(147)I
wherein Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, I is an isotropic phase, and parenthesized values are phase transition temperatures (°C.).

Figure 1:
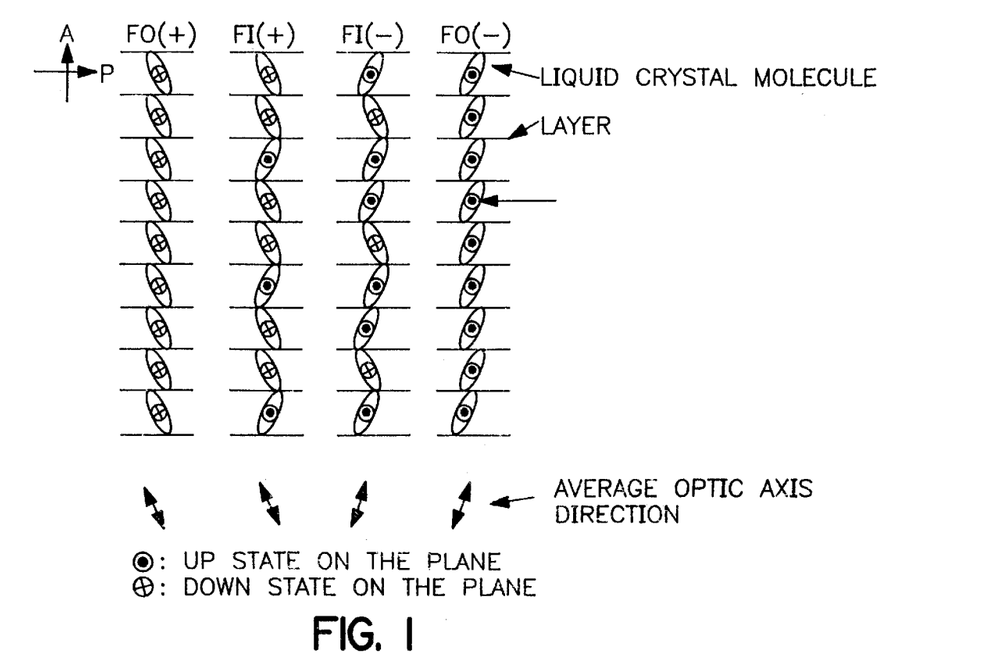
FIG. 1 shows a molecular arrangement state of a ferrielectric phase, in which FI(+) and FI(−) are ferrielectric states and OF(+) and (OF(−) are ferroelectric states.
Figure 2:
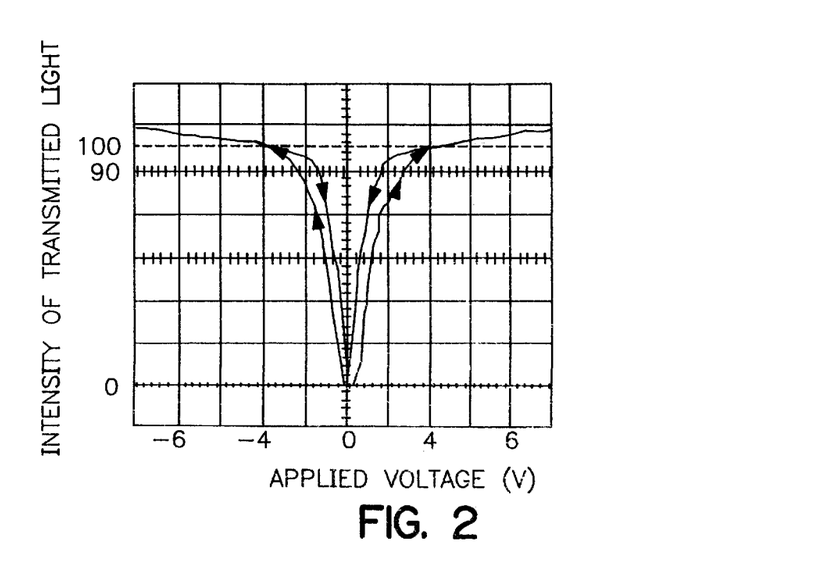
FIG. 2 shows an optical response of a ferrielectric phase to a triangular wave.

For explaining the ferrielectric liquid crystal, FIG. 1 shows a molecular arrangement state of the ferrielectric phase, and FIG. 2 shows an optical response of the ferrielectric phase to a triangular wave.

The ferrielectric phase has a molecular arrangement FI(+) or FI(−) as shown in FIG. 1. In a state where no electric field is present, FI(+) and FI(−) are co-present since FI(+) and FI(−) are equivalent. Average optic axes are therefore in the direction of a layer normal, and a dark state is brought under the condition of polarizers shown in FIG. 1.

The above state corresponds to a site where an applied voltage is 0 and the intensity of transmittance is 0 in FIG. 2.

Further, each of FI(+) and FI(−) has spontaneous polarization as is clear in molecular arrangement states, and in a state where these are co-present, the spontaneous polarizations are cancelled, which causes an average spontaneous polarization of zero. Like an anti-ferroelectric phase, the ferrielectric phase is therefore free from an image sticking phenomenon found in a ferroelectric liquid crystal.

As an electric field is applied to a ferrielectric liquid crystal, a domain having an extinguished position appears at a voltage lower than that at which a ferroelectric state is reached. This shows that the domain has an optic axis in a direction tilted apart from the direction of a layer normal although it is not so tilted as in a ferroelectric state. The above intermediate state is considered to be FI(+) or FI(−). In this case, not a continuous change but a stepwise change in the intensity of transmittance could be observed between voltages 0V and 4V in FIG. 2. In FIG. 2, however, a continuous change in the intensity of transmittance was observed. This is presumably because the threshold voltage of FI(+)→FO(+) or FI(−)→FO(−) is not clear.

In the present invention, a liquid crystal phase in which the above intermediate state is always observed refers to a ferrielectric phase, and a liquid crystal compound in which the temperature range of the ferrielectric phase is the broadest among liquid crystal phases refers to a ferrielectric liquid crystal.

When the applied voltage is further increased, the ferrielectric phase causes phase transition to a ferroelectric phase FO(+) or FO(−), which is a stable state, depending upon a direction of an electric field. That is, in FIG. 2, a phase in which the intensity of transmittance is brought into a saturated state (left and right flat portions in FIG. 2) is FO(+) or FO(−).

It is seen in FIG. 1 that the above ferroelectric state FO(+) or FO(−) has a greater spontaneous polarization than the ferrielectric state FI(+) or FI(−). As explained above, in the ferrielectric phase, a state where FI(+) and FI(−) are co-present is used as "dark", and ferroelectric states FO(+) and FO(−) are used as "light".

A conventional ferroelectric liquid crystal permits switching between FO(+) and FO(−), while a ferrielectric phase has a major characteristic feature in that it permits switching among four states, FO(+), FI(+), FI(−) and FO(−).

Meanwhile, the principle of each liquid crystal display uses birefringence of a liquid crystal, and a display device of which the viewing angle dependency is small can be fabricated.

As shown in FIG. 2, generally, the ferrielectric phase has a small difference between the voltage required for a change from a ferrielectric state to a ferroelectric state and the voltage required for a change from a ferroelectric state to a ferrielectric state. That is, the characteristics of the ferrielectric phase is that it has a strong tendency that the width of its hysteresis is narrow and that it shows a V-letter-shaped optical response, and the ferrielectric phase is suitable for AM driving and a gray-scaling display in AM driving. Further, in a change based on voltage, the ferrielectric liquid crystal has a tendency that the threshold voltage for a change from a ferrielectric state to a ferroelectric state is much smaller than that of an anti-ferroelectric liquid crystal, which also proves that the ferrielectric liquid crystal is suitable for AM driving.

However, few liquid crystal compounds having a ferrielectric phase have been so far synthesized, and none of known liquid crystal compounds having a ferrielectric phase are satisfactory in view of the ferrielectric phase temperature range, hysteresis and threshold voltage when the above liquid crystal compounds alone are applied to an AM drive device.

For example, generally, the drive voltage in an AM drive device is low, and it is required to drive the AM drive device at a high speed at an applied voltage of 10 V or less. When viewed from this aspect, conventionally obtained liquid crystal compounds having a ferrielectric phase have a drawback in response at a drive voltage of 10 V or less, and it has been strongly desired to improve the compounds in this aspect.

The present invention has been made from the above points of view, and it is an object of the present invention to provide a liquid crystal composition which is excellent in driving at a low voltage suitable for use with AM driving and has a novel ferrielectric phase, by incorporating the above optically active compound having the specific structure into a specific ferrielectric liquid crystal compound.

According to the present invention, therefore, there is provided a ferrielectric liquid crystal composition consisting essentially of the optically active compound of the formula (1) and a ferrielectric liquid crystal compound of the formula (3).

wherein, in the formula (1), $R^1$, $X^1$, $X^2$ and m are as defined in the formula (1), and in the formula (3), $R^3$ is a linear alkyl group, each of $W^1$ and $W^2$ is a hydrogen atom or one of these is a hydrogen atom and the other is a fluorine atom, r is an integer of 2 to 4, t is an integer of 2 to 4, and C* is asymmetric carbon atom.

The optically active compound of the formula (1), contained in the above ferrielectric liquid crystal composition of the present invention, is the same as the optically active compound of the formula (1) used in the afore-mentioned anti-ferroelectric liquid crystal composition. In the optically active compound of the formula (1) contained in the ferrielectric liquid crystal composition, $R^1$ is a linear alkyl group, preferably a linear alkyl group having 8 to 10 carbon atoms. m is an integer of 3 to 10, preferably 3 to 8. $X^1$ and $X^2$ are as defined above.

Further, in the ferrielectric compound of the formula (3) contained in the ferrielectric liquid crystal composition, $R^3$ is a linear alkyl group, preferably a linear alkyl group having 7 to 12 carbon atoms. Each of $W^1$ and $W^2$ is a hydrogen atom, or one of these is a hydrogen atom and the other is a fluorine atom. r is an integer of 2 to 4, preferably 3. t is an integer of 2 to 4, preferably 2.

In the ferrielectric liquid crystal composition of the present invention, the proportions of the optically active compound of the formula (1) and the ferrielectric liquid crystal compound of the formula (3) are 1 to 60 mol % and 99 to 40 mol %, preferably 10 to 50 mol % and 90 to 50 mol %.

In the ferrielectric liquid crystal composition of the present invention, preferably, the phase transition temperature of the ferrielectric phase on the high-temperature side is at least 40° C., and the phase transition temperature on the low-temperature side is 0° C. or lower. Particularly preferably, the phase transition temperature on the high temperature side is at least 50° C. Further, in the ferrielectric liquid crystal composition, preferably, a smectic A phase is present at a temperature higher than the temperature at which it shows the ferrielectric phase.

In the ferrielectric phase, further, the threshold voltage for a transition from the ferrielectric phase to the ferroelectric phase is preferably 5 V/μm or less, more preferably 3 V/μm or less.

The above ferrielectric liquid crystal composition of the present invention is used as an active matrix liquid crystal display device by interposing it between substrates provided with non-linear active elements such as thin film transistors or diodes provided for each of pixels. And, the active matrix liquid crystal device can be used as one in which the driving by a voltage of a liquid crystal with non-linear active elements is performed by switching among two ferrielectric states, two ferroelectric states and intermediate states therebetween.

The ferrielectric liquid crystal compound of the general formula (3), used in the present invention, can be easily produced by the method outlined below.

(i) AcO—Ph(X)—COOH+SOCl$_2$→AcO—Ph(X)—COCl (ii) Compound from (i)+CF$_3$C*H (OH)(CH$_2$)$_r$OC$_t$H$_{2t+1}$→AcO—Ph(X)—COO—C*H(CF$_3$)(CH$_2$)$_r$OC$_t$H$_{2t+1}$ (iii) Compound from (ii)+(Ph—CH$_2$NH$_2$) →HO—Ph(X)—COO—C*H(CF$_3$)(CH$_2$)$_r$OC$_t$H$_{2t+1}$ (iv) $R^3$—O—Ph—Ph—COOH+SOCl$_2$→$R^3$—O—Ph—Ph—COCl (v) Compound from (iii)+Compound from (iv) →Ferrielectric liquid crystal In the above (i) to (v), Ph is a 1,4-phenylene group, Ph(X) is a 1,4-phenylene group (which may be substituted with a fluorine atom on its 2- or 3-position), and $R^3$, r and t are as defined in the formula (3).

The above production method is briefly explained as below.

(i) p-Acetoxybenzoic acid is chlorinated with thionyl chloride.

(ii) The chlorinated product from (i) and an optically active alcohol are allowed to react to form an ester.

(iii) The ester from (ii) is deacetylated.

(iv) 4'-Alkyloxybiphenyl-4-carboxylic acid is chlorinated.

(v) The phenol from (iii) and the chlorinated product from (iv) are allowed to react to form a liquid crystal compound.

The novel ferrielectric liquid crystal composition consisting essentially of the optically active compound of the formula (1) and the ferrielectric liquid crystal compound of the formula (3) has a ferrielectric phase in a wide temperature range and exhibits a fast response at a temperature lower than room temperature, and it therefore has an excellent value as a material for a liquid crystal display device.

EXAMPLES

The present invention will be further specifically explained with reference to Examples, while the present invention shall not be limited thereto.

Example 1

(Formula (1): $R^1=C_9H_{19}$, $X^1=H$, $X^2=F$, m=5 (E1)) Preparation of (+)-4-(1-methylhexyloxy)phenyl=2'-fluoro-4'-decanoyloxyphenylbenzoate (1) Preparation of 1-methylhexyl (+)-p-toluenesulfonate A reactor was charged with 3.48 g of R-(-)-2-heptanol and 15 ml(milliliters) of pyridine, and the mixture was cooled to -20° C. While the mixture was stirred, 6.3 g of p-toluenesulfonyl chloride was added at a time, the mixture was stirred at this temperature for 30 minutes, and then, the stirring was continued for further 4 hours at room temperature. The reaction mixture was poured into ice water and extracted with dichloromethane. An organic layer was washed with water and dried over anhydrous sodium sulfate. The solvent was distilled off to give 6 g (yield 74%) of the end product.

(2) Preparation of (+)-4-benzyloxyphenyl-1-methylhexyl ether

A reactor was charged with 6 g of the 1-methylhexyl (+)-p-toluenesulfonate obtained in (1), 4.47 g of hydroquinone monobenzyl ether, 2.38 g of potassium hydroxide and 28 ml of ethanol, and the mixture was stirred at room temperature for 2 hours. Then, the mixture was further refluxed under heat for 1 hour. The reaction mixture was poured into water and extracted with dichloromethane, and an organic layer was washed with 1N hydrochloric acid and with water, and dried over anhydrous sodium sulfate. The solvent was distilled off to give a crude product. The crude product was purified by silica gel column chromatography (eluent; hexane/ethyl acetate=925/75) to give 14.9 g (yield 67%) of the end product.

(3) Preparation of (+)-4-(1-methylhexyloxy)phenol

A reactor was charged with 0.2 g of a 10% palladium-carbon catalyst and then, the atmosphere in the system was purged with nitrogen gas. 4.46 Grams of the benzyl ether obtained in (2) and 30 ml of ethanol were added thereto, and the atmosphere in the system was purged with hydrogen gas. While hydrogen gas was fed through a gas buret, the mixture was allowed to react for 8 hours. The atmosphere in the system was purged with nitrogen gas and then, the catalyst was separated off by filtration, and the solvent was distilled off to give 3 g (yield 97%) of the end product.

(4) Preparation of (+)-4-(1-methylhexyloxy)phenyl=2'-fluoro-4'-decanoyloxyphenylbenzoate A reactor was charged with 1.04 g of 2-fluoro-4-decanoyloxybenzoic acid and 20 ml of thionyl chloride, and the mixture was refluxed under heat for 4 hours. Excessive thionyl chloride was distilled off under reduced pressure. The residue was dissolved in toluene, and washed with hydrochloric acid, with a sodium hydroxide aqueous solution and with water in this order. The solvent was distilled off, and the resultant crude product was purified by silica gel column chromatography (eluent; hexane/ethyl acetate=94/6).

The yield of the product was 0.63 g (yield 61%).

Examples 2 and 3

(Formula (1): $R^1=C_9H_{19}$, $X^1=H$, $X^2=F$, m=3 (E2)) Preparation of (+)-4-(1-methylbutyloxy)phenyl=2'-fluoro-4'-decanoyloxyphenylbenzoate, and (Formula (1): $R^1=C_9H_{19}$, $X^1=H$, $X^2=F$, m=7 (E3)) Preparation of (+)-4-(1-methyloctyloxy)phenyl=2'-fluoro-4'-decanoyloxyphenylbenzoate The end products were obtained in the same manner as in Example 1 except that the R-(-)-2-heptanol used in Example 1 was replaced with R-(-)-pentanol or R-(-)-nonanol.

Example 4

(Formula (1): $R^1=C_9H_{19}$, $X^1=H$, $X^2=H$, m=5 (E4)) Preparation of (+)-4-(1-methylhexyloxy)phenyl=4'-decanoyloxyphenylbenzoate The end product was obtained in the same manner as in Example 1 except that the 2-fluoro-4-decanoyloxybenzoic acid used in Example 1 was replaced with 4-decanoyloxybenzoic acid.

Example 5

(Formula (1): $R^1=C_{10}H_{21}$, $X^1=H$, $X^2=H$, m=5 (E5)) Preparation of (+)-4-(1-methylhexyloxy)phenyl=4'-undecanoyloxyphenylbenzoate The end product was obtained in the same manner as in Example 4 except that the 4-decanoyloxybenzoic acid used in Example 4 was replaced with 4-undecanoyloxybenzoic acid.

Example 6

(Formula (1): $R^1=C_6H_{13}$, $X^1=H$, $X^2=F$, m=5 (E6)) Preparation of (+)-4-(1-methylhexyloxy)phenyl=4'-heptanoyloxy-2'-fluorobenzoate The end product, (+)-4-(1-methylhexyloxy)phenyl=4'-heptanoyloxy-2'-fluorobenzoate, was obtained in the same manner as in Example 1 except that the 2-fluoro-4-decanoyloxybenzoic acid used in Example 1 was replaced with 2-fluoro-4-heptanoyloxybenzoic acid.

Example 7

(Formula (1): $R^1=C_9H_{19}$, $X^1=f$, $X^2=H$, m=5 (E7)) Preparation of (+)-4-(1-methylhexyloxy)phenyl=4'-decanoyloxy-3'-fluorobenzoate The end product, (+)-4-(1-methylhexyloxy)phenyl=4'-decanoyloxy-3'-fluorobenzoate, was obtained in the same manner as in Example 1 except that the 2-fluoro-4-decanoyloxybenzoic acid used in Example 1 was replaced with 3-fluoro-4-decanoyloxybenzoic acid.

Table 1 shows NMR spectrum data of the end products obtained in Examples 1 to 7.

Further, liquid crystal phases were identified by texture observation and DSC (differential scanning calorimeter). Table 2 shows the results, and structural formulae of the compounds (E1) to (E7) are shown subsequently to the above Table 2.

TABLE 1

| Hydrogen atom No. | 1 | 2 | 3 | 4 | 5 | 6 | 7 | 8 | 9 |
|---|---|---|---|---|---|---|---|---|---|
| E1 (δ, ppm) | 0.9 | 2.6 | 7.0 | 7.0 | 8.2 | 7.2 | 6.9 | 4.3 | 0.9 |
| E2 | 0.9 | 2.6 | 7.0 | 7.0 | 8.2 | 7.2 | 6.9 | 4.4 | 0.9 |
| E3 | 0.9 | 2.6 | 7.0 | 7.0 | 8.2 | 7.2 | 6.9 | 4.4 | 0.9 |
| E4 | 0.9 | 2.6 | 7.3 | 8.2 | 7.1 | 6.9 | 4.4 | 0.9 | — |
| E5 | 0.9 | 2.6 | 7.3 | 8.2 | 7.1 | 6.9 | 4.4 | 0.9 | — |
| E6 | 0.9 | 2.6 | 7.0 | 7.0 | 8.1 | 7.1 | 6.9 | 4.4 | — |
| E7 | 0.9 | 2.6 | 8.0 | 7.3 | 8.0 | 7.1 | 6.9 | 4.3 | — |

TABLE 2

| Compound No. | Phase sequence |
|---|---|
| E1 | I(22)SA(-9)Cr |
| E2 | I(22)SA(-1)Cr |
| E3 | I(20)SA(-7)Cr |
| E4 | I(27)SA(17)Cr |
| E5 | I(30)SA(22)Cr |
| E6 | I(9)Cr |
| E7 | I(8.8)Cr |

In the above phase sequences, parenthesized values show transition temperatures (unit; °C.), I is an isotropic phase, SA is a smectic A phase, and Cr is a crystal phase.

Examples 8–10

The optically active compound (E1) obtained in Example 1 in an amount of 10 mol %, 20 mol % or 30 mol % was mixed with an anti-ferroelectric liquid crystal (2A) having the following chemical formula, to obtain compositions.

wherein Ph is a 1,4-phenylene group, Ph(3F) is a 1,4-phenylene group having a fluorine atom substituted on the 3-position (=Y), and C* is asymmetric carbon atom.

Examples 11 and 12

The anti-ferroelectric liquid crystal (2A) used in Example 8 was mixed with 30 mol % of the optically active compound (E4) obtained in Example 4 or with 23 mol % of the optically active compound (E5) obtained in Example 5, to obtain compositions.

Examples 13 and 14

The anti-ferroelectric liquid crystal (2A) used in Example 8 was mixed with 30 mol % of the optically active compound (E6) obtained in Example 6 or with 30 mol % of the optically active compound (E7) obtained in Example 7, to obtain compositions.

Example 15

An anti-ferroelectric liquid crystal (2B) having the following chemical formula was mixed with 30 mol % of the optically active compound (E6) obtained in Example 6, to obtain a composition.

The liquid crystal compositions obtained in Examples 6 to 15 were identified for phases, and measured for response times. Table 3 shows the results.

The liquid crystal phases of the compositions were identified by texture observation and DSC (differential scanning calorimeter).

Further, the response times were measured as follows.

A liquid crystal cell (cell thickness 1.8 μm) having a rubbed polyimide thin film and ITO electrode was filled with a composition in an isotropic state. The cell was gradually cooled at a rate of 1° C./minute to align the liquid crystal in a smectic A phase (SA phase). The cell was placed between polarizer plates crossing each other at right angles, such that the layer direction of the liquid crystal was in parallel with an analyzer or a polarizer.

The minimum intensity of transmitted light was taken as 0%, and the maximum intensity thereof was taken as 100%. While a step voltage having a frequency of 10 Hz and a voltage of 50 V was applied to the liquid crystal cell, the time required for the intensity of transmitted light changing to 90% at the time of switching from an anti-ferroelectric state to a ferroelectric state was taken as response time I, and the time required for the intensity of transmitted light changing to 90% at the time of switching from a ferroelectric state to an anti-ferroelectric state was taken as response time II. These response times were measured. The measurements were all conducted at 10° C.

E1: $C_9H_{19}$—COO—Ph(2F)—COO—Ph—O—C*H($CH_3$)$C_5H_{11}$

3A: $C_9H_{19}$—O—Ph—Ph—COO—Ph(3F)—COO—C*H($CF_3$)($CH_2$)$_3$O$C_2H_5$ wherein Ph is a 1,4-phenylene group, Ph(2F) is a 1,4-phenylene group having a fluorine atom substituted on the 2-position ($X^2$), Ph(3F) is a 1,4-phenylene group having a fluorine atom substituted on the 3-position ($W^2$), and C* is asymmetric carbon atom.

Examples 18 and 19

A phenyl ester compound having the following chemical structure (E2 or E3) in an amount of 40 mol % was mixed with the same ferrielectric liquid crystal (3A) as that used in Example 16.

E2: $C_9H_{19}$—COO—Ph(2F)—COO—Ph—O—C*H($CH_3$)$C_3H_7$

E3: $C_9H_{19}$—COO—Ph(2F)—COO—Ph—O—C*H($CH_3$)$C_7H_{15}$

The compositions obtained in Examples 16 to 19 were identified for phases and measured for response times. Table 4 shows the results.

The liquid crystal composition was identified for liquid crystal phases by texture observation, conoscopic image observation, DSC (differential scanning calorimeter) measurement, and confirmation of a domain having an extinguished position between the direction of a layer nor-

TABLE 3

| Example No. | Composition and Molar ratio | Phase sequence | Response time I | Response time II | Measurement temperature |
|---|---|---|---|---|---|
| 8 | 2A/E1 = 90/10 | I(77)SA(67)SCA*(<−10)Cr | 70 | 58200 | 10° C. |
| 9 | 2A/E1 = 80/20 | I(75)SA(59)SCA*(<−10)Cr | 49 | 72400 | 10° C. |
| 10 | 2A/E1 = 70/30 | I(72)SA(52)SCA*(<−10)Cr | 40 | 74500 | 10° C. |
| 11 | 2A/E4 = 70/30 | I(75)SA(57)SCA*(<−10)Cr | 47 | 69000 | 10° C. |
| 12 | 2A/E5 = 77/23 | I(75)SA(52)SCA*(<−10)Cr | 45 | 13100 | 10° C. |
| 13 | 2A/E6 = 70/30 | I(75)SA(51)SCA*(<−50)Cr | 39 | 2600 | 10° C. |
| 14 | 2A/E7 = 70/30 | I(69)SA(53)SC*(50)SCA*(<−50)Cr | 62 | 5400 | 10° C. |
| 15 | 2B/E6 = 70/30 | I(81)SA(55)SCA*(<−20)Cr | 44 | 7635 | 10° C. |
| Compound 2A | | I(83)SC*(77)SCA*(<−50)Cr | 79 | 20200 | 10° C. |
| Compound 2B | | I(90)SCA*(<−20)Cr | 141 | 7635 | 10° C. |

In Table 3, in "Phase sequence", parenthesized values show transition temperatures (°C.), I is an isotropic phase, SA is a smectic A phase, SCA* is an anti-ferroelectric phase, SC* is a ferroelectric phase, and Cr is a crystal phase.

Further, the unit in "Response time I" and "Response me II" is μ second.

Examples 16 and 17

A phenyl ester compound (E1) having the following chemical structure in an amount of 30 mol % or 40 mol % was mixed with a ferrielectric liquid crystal (3A) having the following chemical structure.

mal and the direction of an optic axis in a ferroelectric state (observation of a intermediate state FI(±)).

The observation of a conoscopic image is effective means of identifying a ferrielectric phase. The conoscopic image observation was conducted according to a piece of literature (J. Appl. Phys. 31, 793 (1992)).

On the basis of the texture observation by general parallel alignment cell and the conoscopic image observation and DSC measurement, and on the basis of the observation of an intermediate state, i.e., an observed domain having an extinguished position between the direction of a layer normal and the direction of an optic axis in a ferroelectric state, the phase sequence of the liquid crystal compositions in Examples were identified.

A cell for measuring the optical response was prepared in the following procedures.

Glass plates with insulating film (SiO$_2$, thickness; 50 nm) and ITO electrodes were coated with polyimide (thickness; about 80 nm), and one of a pair of the glass plates was rubbed. The pair of glass plates were attached to each other through a spacer having a particle diameter of 1.6 μm to form a test cell. The cell thickness was 2 μm. The liquid crystal composition was heated until the liquid crystal showed an isotropic phase and then, the liquid crystal was injected into the test cell by capillarity. Then, the cell was gradually cooled at a rate of 1° C./minute to align the liquid crystal in parallel.

Then, the test cell was driven by applying a triangular wave voltage of ±10 V, 50 mHz, to the test cell to study a change in transmitted light.

When the minimum intensity of the transmitted light was taken as 0% and the maximum intensity of the transmitted light was taken as 100%, the voltage at which the intensity of transmitted light became 90% by phase transition from a ferrielectric phase to a ferroelectric phase was defined as threshold voltage I (unit: V/μm), and the voltage at which the intensity of transmitted light became 90% by phase transition from a ferroelectric phase to a ferrielectric phase was defined as threshold voltage II (unit: V/μm).

Further, the time required for a change in the intensity of transmitted light by 90% under the application of a 8 V pulse voltage having a frequency of 10 Hz was defined as a response time, and the response time was measured.

TABLE 4

| Phase sequence | Threshold voltage I | Threshold voltage II | Response time (μs) | Measurement temperature |
|---|---|---|---|---|
| Ex. 16 | Cr(<−10)SCγ*(68)SA(87)I | 1.3 | 1.2 | 64 | 30° C. |
| Ex. 17 | Cr(<−10)SCγ*(55)SA(82)I | 1.2 | 1.1 | 41 | 30° C. |
| Ex. 18 | Cr(<−10)SCγ*(52)SA(86)I | 1.2 | 1.2 | 50 | 30° C. |
| Ex. 19 | Cr(<−10)SCγ*(54)SA(79)I | 1.3 | 1.1 | 45 | 30° C. |
| Cpd E1 | Cr(25)I | | | | |
| Cpd E2 | Cr(37)I | | | | |
| Cpd E3 | Cr(5)SA(20)I | | | | |
| Lpd 3A | Cr(34)SCγ*(101)SA(103)I | 1.3 | 1.0 | 100 | 40° C. |

In Table 4, "Cpd" stands for optically active compound and "Lpd" stands for liquid crystal compound. In "Phase sequence", parenthesized values show transition temperatures (°C.), Cr is a crystal phase, SCγ* is a ferrielectric phase, SA is a smectic A phase, and I is an isotropic phase.

What is claimed is:

1. An optically active compound of the formula (1), wherein R$^1$ is a linear alkyl group, one of X$^1$ and X$^2$ is a hydrogen atom and the other is a fluorine atom, m is an integer of 3 to 10, and C* is an asymmetric carbon atom.

2. The optically active compound of claim 1, wherein R$^1$ in the formula (1) is a linear alkyl group having 6 to 12 carbon atoms.

3. An anti-ferroelectric liquid crystal composition consisting essentially of an optically active compound of the formula (1) and an anti-ferroelectric liquid crystal compound of the formula (2), wherein, in the formula (1), R$^1$ is a linear alkyl group, one of X$^1$ and X$^2$ is a hydrogen atom and the other is a fluorine atom, m is an integer of 3 to 10, and C* is an asymmetric carbon atom, and in the formula (2), R$^2$ is a linear alkyl group, each of Z$^1$ and Z$^2$ is a hydrogen atom or one of Z$^1$ and Z$^2$ is a hydrogen atom and the other is a fluorine atom, p is an integer of 5 to 8, q is an integer of 2 or 4, and C* is an asymmetric carbon atom.

4. The anti-ferroelectric liquid crystal composition of claim 3, wherein R$^1$ in the formula (1) is a linear alkyl group having 6 to 12 carbon atoms, and m is an integer of 3 to 8.

5. The anti-ferroelectric liquid crystal composition of claim 3, wherein R$^2$ in the formula (2) is a linear alkyl group having 6 to 10 carbon atoms.

6. The anti-ferroelectric liquid crystal composition of claim 3, wherein Z$^1$ in the formula (2) is a hydrogen atom and Z$^2$ is a fluorine atom.

7. The anti-ferroelectric liquid crystal composition of claim 3, wherein q in the formula (2) is 2.

8. The anti-ferroelectric liquid crystal composition of claim 3, which contains 5 to 40 mol % of the optically active compound of the formula (1) and 95 to 60 mol % of the liquid crystal compound of the formula (2).

9. The anti-ferroelectric liquid crystal composition of claim 3, which has an upper limit temperature of an anti-ferroelectric phase at 40° C. or higher and a lower limit temperature of an anti-ferroelectric phase at 0° C. or lower.

10. The anti-ferroelectric liquid crystal composition of claim 3, wherein the composition has a smectic A phase at a temperature higher than a temperature at which the composition has an anti-ferroelectric phase.

11. A ferrielectric liquid crystal composition consisting essentially of an optically active compound of the formula (1) and a ferrielectric liquid crystal compound of the formula (3), wherein, in the formula (1), R$^1$ is a linear alkyl group, one of X$^1$ and X$^2$ is a hydrogen atom and the other is a fluorine atom, m is an integer of 3 to 10, and C* is an asymmetric carbon atom, and in the formula (3), R$^3$ is a linear alkyl group, each of W$^1$ and W$^2$ is a hydrogen atom or one of these is a hydrogen atom and the other is a fluorine atom, r is an integer of 2 to 4, t is an integer of 2 to 4, and C* is asymmetric carbon atom.

12. The ferrielectric liquid crystal composition of claim 11, wherein R$^1$ in the formula (1) is a linear alkyl group having 6 to 10 carbon atoms and m is an integer of 3 to 8.

13. The ferrielectric liquid crystal composition of claim 11, wherein R$^3$ in the formula (3) is a linear alkyl group having 7 to 12 carbon atoms.

14. The ferrielectric liquid crystal composition of claim 11, wherein r in the formula (3) is 3 and t is 2.

15. The ferrielectric liquid crystal composition of claim 11, which contains 1 to 60 mol % of the optically active compound of the formula (1) and 99 to 40 mol % of the ferrielectric liquid crystal compound of the formula (3).

16. The ferrielectric liquid crystal composition of claim 11, wherein a transition temperature of a ferrielectric phase is at 40° C. or higher on a high temperature side and at 0° C. or lower on a low temperature side.

17. The ferrielectric liquid crystal composition of claim 11, wherein the composition has a smectic A phase at a temperature higher than that of a ferrielectric phase.

18. The ferrielectric liquid crystal composition of claim 11, which has a threshold voltage for transition from a ferrielectric phase to a ferroelectric phase of 5 V/$\mu$m or less.

19. A simple matrix liquid crystal display device obtained by interposing the anti-ferroelectric liquid crystal composition of claim 3 between substrates provided with scanning electrodes and signal electrodes arranged in a matrix form.

20. The simple matrix liquid crystal display device of claim 19, wherein the device driven by a voltage is carried out by switching among one anti-ferroelectric state and two ferroelectric states.

21. An active matrix liquid crystal display device obtained by interposing the ferrielectric liquid crystal composition of claim 11 between substrates provided with non-linear active elements provided for each of pixels.

22. The active matrix liquid crystal display device of claim 21, wherein the device having the non-linear active elements is driven under an applied voltage by switching among two ferrielectric states, two ferroelectric states and intermediate states thereof.

* * * * *